US010766648B2

(12) United States Patent
Dowdle et al.

(10) Patent No.: US 10,766,648 B2
(45) Date of Patent: Sep. 8, 2020

(54) PROPELLANT FILLING APPARATUS

(71) Applicant: MEXICHEM FLUOR S.A. DE C.V., San Luis Potosi (MX)

(72) Inventors: Paul Alan Dowdle, Runcorn (GB); Stuart Corr, Runcorn (GB); Paul Watkinson, Runcorn Chshire (GB)

(73) Assignee: MEXICHEM FLUOR S.A. DE C.V., San Luis Potosi (MX)

( * ) Notice: Subject to any disclaimer, the term of this patent is extended or adjusted under 35 U.S.C. 154(b) by 0 days.

(21) Appl. No.: 16/336,254

(22) PCT Filed: Sep. 18, 2017

(86) PCT No.: PCT/GB2017/052755
§ 371 (c)(1),
(2) Date: Mar. 25, 2019

(87) PCT Pub. No.: WO2018/060677
PCT Pub. Date: Apr. 5, 2018

(65) Prior Publication Data
US 2019/0241294 A1   Aug. 8, 2019

(30) Foreign Application Priority Data

Sep. 29, 2016   (GB) .................................. 1616581.3

(51) Int. Cl.
*B65B 31/10*   (2006.01)
*B65B 55/02*   (2006.01)
(Continued)

(52) U.S. Cl.
CPC ......... *B65B 31/003* (2013.01); *A61M 15/009* (2013.01); *B65B 31/10* (2013.01);
(Continued)

(58) Field of Classification Search
CPC ..... B65B 31/003; B65B 55/027; B65B 57/14; B65B 31/10; B65B 31/02; F24F 3/1607;
(Continued)

(56) References Cited

U.S. PATENT DOCUMENTS 3,545,170 A * 12/1970 Leonard ................ B65B 31/003
                                                 53/88
4,474,199 A    10/1984 Blaudszun
(Continued)

FOREIGN PATENT DOCUMENTS

AU          3906672 A    8/1973
CA          1198396      12/1985
(Continued)

OTHER PUBLICATIONS

International Preliminary Report on Patentability issued in PCT/GB2017/052755 dated Apr. 2, 2019.
(Continued)

*Primary Examiner* — Timothy L Maust
*Assistant Examiner* — Jason K Niesz
(74) *Attorney, Agent, or Firm* — Ryan Kromholz & Manion, S.C.

(57) ABSTRACT

A propellant filling apparatus (10) comprising a filling booth (11) for receiving within it one or more containers for filling with a propellant; a propellant inlet (12) to the filling booth (11) that is capable of supplying propellant into one or more containers within the filling booth (11) from a propellant supply; an inert gas inlet (13) supplying inert gas from an inert gas supply (14) into the filling booth (11), a discharge outlet (16) from the filling booth (11); an extraction fan (17) that is capable of adjusting its fan speed to maintain the pressure of gas in the filling booth (11) to be lower than atmospheric pressure; and an oxygen detector (27) that is capable of detecting levels of oxygen in the filling booth (11)
(Continued)

and triggering circulation of inert gas in the filling booth (11) when the level of oxygen in the filling booth (11) falls below an oxygen threshold level.

30 Claims, 1 Drawing Sheet

(51) Int. Cl.
    *B65B 57/14*     (2006.01)
    *B65B 31/00*     (2006.01)
    *A61M 15/00*     (2006.01)
    *F24F 3/16*     (2006.01)

(52) U.S. Cl.
    CPC ............ *B65B 55/027* (2013.01); *B65B 57/14* (2013.01); *F24F 3/1607* (2013.01); *A61M 2209/045* (2013.01)

(58) Field of Classification Search
    CPC .......... A61M 15/009; A61M 2209/045; B08B 15/023; B08B 15/00
    See application file for complete search history.

(56) References Cited

U.S. PATENT DOCUMENTS 5,685,771 A     11/1997   Kleppen
6,138,720 A *  10/2000   Zeigler ................. B65B 31/003
                                                141/18

FOREIGN PATENT DOCUMENTS

WO     WO2004/080540     9/2004
WO     WO2009/018990     2/2009

OTHER PUBLICATIONS

Search Report from UK IPO dated Feb. 21, 2017, cited in corresponding application GB1616581.3.
International Search Report issued in WO2018/060677 dated Jan. 22, 2018.
Written Opinion issued in WO2018/060677 dated Jan. 22, 2018.

* cited by examiner

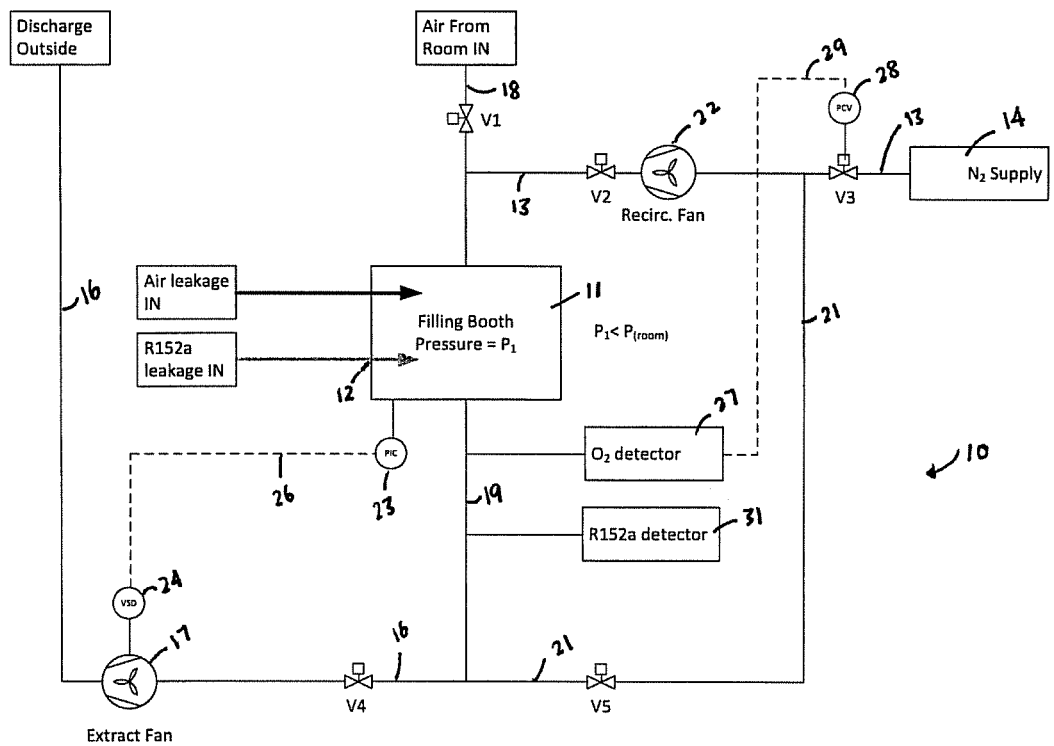

PROPELLANT FILLING APPARATUS

This invention relates to a propellant filling apparatus and its method of operation.

Propellants are widely use in the pharmaceutical, household and cosmetic aerosol industries.

In the pharmaceutical industry, inhalation aerosols also known as Metered Dose Inhalers (MDIs) provide an effective method of delivering medication in an atomised form. Propellants are used to force the medication out of a container through a nozzle or similar atomising outlet. The invention as defined herein is of particular benefit in the handling of propellants in MDI filling apparatuses. It is additionally of benefit in other propellant filling situations.

Chlorofluorocarbons (CFCs) previously were often used as propellants but since the Montreal Protocol came into force in 1989, they have been replaced in nearly every country due to the negative effects CFCs have on the Earth's ozone layer. Whilst many household and consumer aerosols have transitioned to hydrocarbon (HC) propellants, the particular requirements of the medical aerosols sector, and especially inhalation aerosols such as asthma inhalers, require the use of the non-flammable hydrofluorocarbons (HFCs): either HFC 134a (1,1,1,2,-tetrafluoroethane) or HFC 227 (1,1,1,2,3,3,3-heptafluoropropane) or combinations of the two.

There is growing concern that many HFCs have high global warming potential (GWP) and also an interest in adopting reduced-GWP HFCs where possible. Examples of HFCs that have relatively low global warming potential when compared to other HFCs include R32 (difluoromethane), R152a (1,1-difluoroethane), R1234yf (1,1,1,2-tetrafluoropropene), R1234ze(E) and (Z) (1,1,1,3-tetrafluoropropene) and the HCFC R1233zd(E) (trans-1-chloro-3,3,3-trifluoropropene). However with the exception of R1233zd (E) all of these reduced GWP fluids are flammable to a degree. This flammability creates challenges, in particular with regard to storage and also to the handling of the propellant in production situations, particularly in so-called "current good manufacturing practice" (cGMP) environments. The invention seeks to address such problems.

According to an aspect of the invention, there is provided a propellant filling apparatus comprising a filling booth for receiving within it one or more containers for filling with a propellant; a propellant inlet to the filling booth that is capable of supplying propellant, for filing into one or more containers within the filling booth, from a propellant supply; an inert gas inlet supplying inert gas from an inert gas supply into the filling booth; a discharge outlet from the filling booth; an extraction fan that is capable of adjusting its fan speed to maintain the pressure of gas in the filling booth to be lower than atmospheric pressure outside the filling booth; and an oxygen detector that is capable of detecting levels of oxygen in the filling booth and triggering circulation of inert gas in the filling booth when the level of oxygen in the filling booth attains or exceeds an oxygen threshold level that is proportional to the maximum oxygen concentration of the propellant.

In use the apparatus of the invention permits the controlled introduction of an inert gas into an enclosed volume (i.e. the filling booth) containing a flammable component such as but not limited to a propellant. This reduces the oxygen level in the enclosed volume and therefore reduces the risk of an explosion or ignition event occurring. In this regard, for a variety of reasons ambient air may leak into the filling booth, with the result that oxygen levels may rise above a safety threshold, giving rise to an explosion or ignition risk. The invention prevents such increases in oxygen content from occurring.

As used herein references to "oxygen levels" are to concentrations of oxygen in e.g. the enclosed volume defined by the filling booth. Similarly, references to levels of inert gas and levels of propellant are references to concentration levels within e.g. a volume such as that of the filling booth.

The propellant filling apparatus as defined above is further advantageous because it controls the introduction of inert gas to only those times in a filling process that have the highest risk (for example during start up and shut down) and also controls the levels of inert gas. This leads to minimising of the consumption of the inert gas, thereby reducing costs. An additional advantage is that through use of the apparatus the volume of a production area that is supplied with inert gas is kept to a minimum, thereby improving operator safety.

Furthermore the extraction fan, by controlling the pressure in the booth such that it is lower than atmospheric pressure, ensures that there is no leakage of inert gas or propellant from the booth into the room or factory space where the apparatus is located. This is desirable since it protects operators in the room from, for example, oxygen depletion due to increases in amounts of inert gas in the room.

It is preferable if the propellant filling apparatus further comprises a propellant detector that is capable of detecting levels of propellant in the filling booth and triggering the circulation of inert gas in the filling booth when the level of propellant in the filling booth rises above a propellant threshold level.

The propellant detector provides an additional means of ensuring that the level of propellant in the filling booth does not exceed a level which may create a risk of explosion or ignition in the filling booth.

The propellant may be a flammable gas. The flammable propellant will preferably comprise one or more of R32 (difluoromethane), R152a (1,1-difluoroethane), R1234yf (1,1,1,2-tetrafluoropropene), R1234ze(E) and (Z) (1,1,1,3-tetrafluoropropene) and the HCFC R1233zd(E) (trans-1-chloro-3,3,3-trifluoropropene). More preferably the propellant will comprise R32 and/or R152a and more preferably will consist essentially of R32 and/or R152a. By consisting essentially of we mean that the propellant contains at least 95% by weight, more preferably 98% by weight and even more preferably at least 99% by weight of the specified propellant component(s). The propellant preferably has a global warming potential (GWP) of below 1000, more preferably below 700 and especially preferably below 150.

The propellant may include other non-propellant species such as solvents, surfactants, lubricants and other excipients commonly used in the art including but not limited to ethanol, glycerol and surfactants such as oleic acid, lecithin and polyvinylpyrrolidone (PVP). Further, the propellant may include minor quantities of one or more active pharmaceutical ingredients (APIs) either in solution or suspension in the propellant.

References to the term "propellant" in the description hereof refer typically to unadulterated propellants (such as R32 and/or R152a). Such propellants may alternatively be present in mixtures containing, for example, components such as polar excipients/co-solvents such as ethanol, drugs and surfactants typically in small amounts as would be understood by the person of skill in the art.

It is beneficial to the environment to use a propellant (or propellant mixture) comprising R32 and/or R152a because it has an ozone depletion potential of zero, and a lower global warming potential and a shorter atmospheric lifetime than several other propellant types.

The inert gas may be any non-flammable inert gas with low GWP including nitrogen, and argon.

It is advantageous to use nitrogen for oxygen depletion because it is inert, widely available, and relatively inexpensive compared to other inert gases. Other gases may however be employed for this purpose if desired.

It is preferable if the oxygen threshold level is 9.8%. For increased safety, it is further preferred to maintain an oxygen threshold level of 7.8% or lower.

It is advantageous if the propellant filling apparatus includes a controller for controlling the temperature of the inert gas supply and/or for controlling the humidity of the inert gas supply.

The ability to control the temperature and humidity of the gas supply within a room is desirable to satisfy clean room requirements in the pharmaceutical industry and several other industries in which the invention may be used.

Conveniently, the speed of the extraction fan may be controlled using a pressure controller that measures the pressure of gas in the filling booth (or is operatively connected to a pressure measuring device that generates one or more signals, such as electrical or other physical signals, that indicate the measured pressure and are fed as inputs to the pressure controller) and compares the measured pressure with atmospheric pressure in the vicinity of and external to the filling booth. Preferably the pressure controller also performs an indicator function whereby an operator of the apparatus may visually assess the gas pressure in the filling booth.

It is advantageous if the propellant filling apparatus satisfies cGMP requirements.

According to another aspect of the invention, there is provided a method of operating a propellant filling apparatus, the method comprising the steps of filling one or more containers in a filling booth with a propellant; supplying an inert gas into the filling booth; adjusting the fan speed of an extraction fan to maintain a lower pressure in the filling booth than atmospheric pressure outside the filling booth; detecting levels of oxygen in the filling booth; and circulating the inert gas in the filling booth when the detected level of oxygen in the filling booth attains or exceeds a threshold level corresponding to the maximum oxygen concentration of the propellant.

As used herein the term "filling" is not necessarily intended to imply complete filling of a container or single-step filling; and on the contrary may include e.g. partial filling, stepwise filling involving a number of filling stages, over-filling and/or purging of the container(s).

It is advantageous if the method further comprises the step of detecting the level of inert gas in the filling booth.

There now follows a description of preferred embodiments of the invention, by way of non-limiting example, with reference being made to accompanying FIG. 1 that is a schematic representation of an embodiment of a propellant filling apparatus according to the invention.

FIG. 1 depicts in schematic form a propellant filling apparatus 10 comprising a filling booth 11. The filling booth 11 may be constructed from e.g. five mutually orthogonal walls and a floor that are joined along adjacent edges to define a cuboidal volume inside which filling of containers with propellant is intended to take place. One or more of the filling booth walls may be equipped with an openable door or other opening permitting human access to the cuboidal space. One or more further apertures may be provided in order to permit the infeed of empty containers and the egress of filled containers. The characteristics of the filling booth and substantial parts of the filling apparatus will be known to the person of skill in the art and do not require detailed describing herein.

In use the filling booth 11 receives one or more containers, not depicted, within it for filling with a propellant. In the manufacture of MDIs, the one or more containers is for holding a mixture of insoluble medication suspended in liquefied, pressurised propellant. The filling of other types of containers is also possible using apparatuses and methods according to the invention.

The filling booth 11 is typically located in a clean room or factory space that satisfies cGMP requirements. Additionally, as mentioned, the propellant filling apparatus 10 itself in most embodiments of the invention satisfies cGMP requirements.

The filling booth 11 has a propellant inlet 12, that is capable of supplying propellant for filling into the one or more containers from a propellant supply (labelled "R152a leakage IN" in FIG. 1, although as noted the invention is not limited to the use of R152a, or indeed a single substance, as the propellant), and an inert gas inlet 13 supplying inert gas from an inert gas supply 14 such as but not limited to a gas generator, a cylinder or gas tank into the filling booth 11. The inert gas inlet 13 is a gas supply line that connects the inert gas supply 14 to the filling booth 11.

In FIG. 1 the inert gas supply 14 is labelled "$N_2$ supply". As explained herein the invention is not limited to the use of nitrogen as the inert gas, although in many situations this gas is preferred.

The filling booth 11 is capable of working using e.g. powder-fill, suspension-fill and cold-fill techniques. These techniques are known to the person of skill in the art for filling the containers with propellant and other substances forming the contents of, for example, an MDI.

In the preferred embodiment of the invention, the propellant is R32 and/or R152a. In other embodiments of the invention any of a variety of propellants, including in some cases non-HFC propellants, may be used.

As mentioned, the inert gas can be nitrogen. Nitrogen can be supplied from, for example, a gas generator such as but not limited to a nitrogen pressure swing absorption (PSA) system. The nitrogen produced from the PSA system preferably is filtered to the correct particulate level before it is allowed to be released into the propellant filling apparatus 10.

Other sources of inert gas, especially but not limited to nitrogen, are possible within the scope of the invention.

A discharge outlet 16 allows gas to leave the filling booth 11 and be discharged outside of the propellant filling apparatus 10.

The filling booth 11 is connected by way of the discharge outlet 16 to an extraction fan 17 which is capable of adjusting its fan speed to maintain the pressure of gas in the filling booth 11 to be lower than atmospheric pressure outside the filling booth 11.

An air inlet 18 in the illustrated embodiment also connects to the filling booth 11 via the inert gas inlet 13. The air inlet 18 is controlled by a valve V1 which is further described below. The air inlet 18 allows air from outside the propellant filling apparatus 10 (and labelled "Air from room IN" in FIG. 1) into the filling booth 11.

As illustrated in FIG. 1, a pipe 19 allows gas to leave the filling booth and depending on the settings of various valves that are described below connects to either (i) the extraction fan 17 for discharging via the discharge outlet 16 or (ii) a recirculation pipe 21 which connects to the inert gas inlet 13 leading into the filling booth 11.

A recirculation fan 22 is located in the recirculation pipe 21. When the recirculation fan 22 turns on, inert gas and other gases removed from the filling booth 11 via pipe 19 enter the recirculation pipe 21 and are returned to the filling booth 11. In other words, the recirculation fan 22 recirculates the inert gas which has been released by the inert gas supply 14 into the filling booth 11.

The propellant filling apparatus 10 comprises valves V1 to V5 which control the passage of gas or air in particular directions as follows:

Valve V1, located in the air supply inlet 18, allows/stops inflow of atmospheric air into the filling booth 11;

Valves V2 and V5, located in the recirculation pipe 21, allow/stop recirculation of inert gas;

Valve V3, located in the inert gas inlet 13, allows/stops the flow of inert gas from the inert gas supply 14; and Valve V4, located in the discharge outlet 16, allows/stops discharge of air from the filling booth 11 via the extraction fan 17

The speed of the extraction fan 17 is controlled using a pressure controller. As illustrated in FIG. 1, the pressure controller can be a pressure indicator controller (PIC) 23 which measures and indicates the pressure of gas in the filling booth 11 and allows the speed of the extraction fan 17 to be adjusted via, for example, a Variable Speed Drive (VSD) 24 to maintain the filling booth 11 pressure below atmospheric pressure outside the filling booth 11. The VSD 24 may be connected to the PIC 23 via a pilot line 26 indicated in dotted lines in FIG. 1. Details of the nature and operation of the VSD 24 will be known to the person of skill in the art and therefore do not need to be described in detail herein.

The propellant filling apparatus 10 in accordance with the invention operates within a safety margin determined by the Maximum Oxygen Concentration (MOC) specific to the propellant (or propellant mixture) under consideration. Any concentration below this level can be considered safe. This is because, as mentioned above, if the oxygen level attains or exceeds the MOC there is a risk (which may be a high risk) of an explosion or a fire event occurring.

The basic formula for calculating the MOC is:

$$LEL \times \text{Moles } O_2 = MOC$$

wherein LEL is the Lower Explosion Limit for the flammable propellant in question; and Moles $O_2$ is the number of moles of oxygen which will react with 1 mole of flammable propellant, based upon the stoichiometric equation of combustion.

As an added safety measure, the Recommended Maximum Oxygen Concentration (RMOC) is calculated at 80% of the MOC.

Taking the exemplary embodiment in which the propellant is R152a and the inert gas is nitrogen, the following steps are taken for calculating the RMOC:

1) Determine the stoichiometric number of moles of oxygen required to completely burn 1 mole of R152a with the chemical formula $CH_3CF_2H$.

$$C_2F_2H_4 + 2.5O_2 \rightarrow 2CO_2 + 2HF + H_2O$$

From the above equation, 2.5 moles of oxygen are required to burn 1 mole of R152a.

2) Multiply the number of moles of oxygen obtained in Step 1 by the LEL for R152a. This is the MOC.

The LEL of R152a is 3.9%.

Thus the MOC=3.9×2.5=9.75% in the case of R152a.

The propellant filling apparatus 10 further comprises an oxygen detector 27. The output signal 29 from the oxygen detector determines the position of the inert gas flow control valve V3 under the control of pressure controlled valve (PCV) elements represented by numeral 28. There are many different ways in which the oxygen detector 27 can measure oxygen level and the invention includes measuring oxygen using apparatuses which include zirconia-based sensor elements and/or rely on physical effects such as electrochemical/Galvanic phenomena, infrared energy, ultrasonic energy or laser energy.

The propellant filling apparatus 10 may also comprise a propellant detector 31 that is capable of detecting levels of propellant in the filling booth 11. The propellant detector may be specific to one or more particular kinds of propellant, as indicated by the labelling in FIG. 1. Other types of propellant detector also are possible within the scope of the invention.

The propellant filling apparatus 10 may comprise a controller (not shown in the drawing) for controlling the temperature of the inert gas supply 14.

When the apparatus 10 is not in use, valves V1, V3 and V5 are closed whereas valves V2 and V4 are open.

When an operator desires to use the filling booth 11 to fill one or more containers with propellant, the operator temporarily enters or otherwise accesses the filling booth 11 via, for example, the openable door as described above to place the containers in the filling booth 11.

The propellant filling apparatus 10 is activated with the result that propellant enters the filling booth 11 via the propellant inlet 12. Most of the propellant is filled into the containers using e.g. an indexable filling head but some propellant spillage typically occurs.

To prevent the oxygen level in the filling booth from rising above the MOC and thereby risking the initiation of combustion of the propellant, the operator by opening valve V3 adds inert gas from the inert gas supply into the filling booth 11. Instead of a manual intervention by an operator, an automated control regime can alternatively be implemented to open the valve V3 and/or the other controllable elements described herein, including valves V1, V2, V4 and V5. The elements of a suitable control arrangement will be known to the person of skill in the art.

Indeed all references herein to manual intervention by an operator can be considered alternatively to be suitable for completion using an automated system.

When the operator of the propellant filling apparatus 10 switches on the extraction fan 17, but the recirculation fan 22 is not yet switched on, leakage of air takes place into the filling booth 11. This causes the oxygen level in the vicinity of the propellant in the filling booth 11 to rise, potentially to dangerous levels as described herein.

When however the operator opens valve V3 to allow inert gas to enter the filling booth 11, the extraction fan 17 activates and adjusts its speed to maintain the required filling booth pressure to lower than the atmospheric pressure outside the filling booth 11. This causes purging of the filling booth 11 with inert gas. This reduces the oxygen concentration to safe levels.

Purging is continued for as long as necessary in order to achieve the aforementioned effect.

While effecting filling of the containers within the filling booth 11 with propellant, if required, the operator (or, if present, an automatic control arrangement) can open valve V1 to effectively allow a larger inflow of air into the filling booth 11. The inert gas inflow then increases through operation of components V3 and 28 with the aim of maintaining the oxygen concentration at or below the oxygen threshold level, i.e. the MOC or more preferably the RMOC as explained. The fan speed of the extraction fan 17 also increases to maintain a lower pressure than atmospheric pressure within the filling booth 11. This mode ensures that propellant leaks are not concentrated in the filling booth 11, due to the recirculation effect. This could also be achieved without adding extra air inflow by opening valve V1, increasing the inert gas inflow from the inert gas supply 14 and increasing the speed of the extraction fan 17.

The oxygen detector 27 is capable of detecting levels of oxygen in the filling booth 11 and triggering circulation of inert gas in the filling booth 11 when the level of oxygen in the filling booth 11 falls below the MOC or preferably the RMOC.

When the oxygen detector 27 senses that the level of oxygen in the filling booth 11 has reached or fallen below the oxygen threshold level, the filling booth 11 is considered purged. This triggers the recirculation fan 22 to start and valve V5 is opened so that there is recirculation of the inert gas within the filling booth 11. This leads to control of the overall quantity of inert gas required to maintain the required low level of oxygen concentration.

When purging is no longer needed, in other words when there is no longer a supply of propellant for filling containers within the filling booth 11, valves V2, V3 and V5 close and the recirculation fan 22 is stopped. Valves V1 and V4 open so that air from outside the propellant filling apparatus can displace the inert gas. This step is desirable at the end of the run of the filling operation or if for example an operator needs to access the filling booth 11.

The propellant filling apparatus 10 according to the invention gives rise to numerous advantages, as set out above, compared with the prior art. It is expected to make a significant contribution both to the safety of propellant filling manufacturing and to reducing the cost of manufacture.

For the avoidance of doubt it Is emphasised that the invention includes within its scope both apparatus as claimed and described herein; and methods as described and claimed herein. Such methods may as noted be put into effect through the intervention of a human operator, or through the operation of automated control elements. In the latter case the control elements may operate on the basis of fixed logic such as firmware; or one or more of them may be under the control of a programmable device such as a microprocessor, personal computer or line controller.

Preferences and options for a given aspect, feature or parameter of the invention should, unless the context indicates otherwise, be regarded as having been disclosed in combination with any and all preferences and options for all other aspects, features and parameters of the invention.

The listing or discussion of any apparently prior published document or apparatus in this specification should not necessarily be taken as an acknowledgement that the document or apparatus is part of the state of the art or is common general knowledge.

The invention claimed is:

1. A propellant filling apparatus (10) comprising
a filling booth (11) for receiving within it one or more containers for filling with a propellant;
a propellant inlet (12) to the filling booth (11) that is capable of supplying propellant, for filing into one or more containers within the filling booth (11), from a propellant supply;
an inert gas inlet (13) supplying inert gas from an inert gas supply (14) into the filling booth (11);
a discharge outlet (16) from the filling booth (11);
an extraction fan (17) that is capable of adjusting its fan speed to maintain the pressure of gas in the filling booth (11) to be lower than atmospheric pressure outside the filling booth (11); and
an oxygen detector (27) that is capable of detecting levels of oxygen in the filling booth (11) and triggering circulation of inert gas in the filling booth (11) when the level of oxygen in the filling booth attains or exceeds an oxygen threshold level that is proportional to the maximum oxygen concentration of the propellant.

2. A propellant filling apparatus (10) according to claim 1, further comprising a propellant detector (31) that is capable of detecting levels of propellant in the filling booth (11) and triggering circulation of inert gas in the filling booth (11) when the level of propellant in the filling booth (11) rises above a propellant threshold level.

3. A propellant filling apparatus (10) according to claim 1 supplying in use a said propellant, wherein the propellant is a flammable gas.

4. A propellant filling apparatus (10) of claim 3 wherein the flammable gas comprises one or more of R32 (difluoromethane), R152a (1,1-difluoroethane), R1234yf (1,1,1,2-tetrafluoropropene), R1234ze(E) and (Z) (1,1,1,3-tetrafluoropropene) and the HCFC R1233zd(E) (trans-1-chloro-3,3,3-trifluoropropene).

5. A propellant filling apparatus (10) of claim 3 wherein the flammable gas consists entirely of R32.

6. A propellant filling apparatus (10) of claim 3 wherein the flammable gas comprises at least 95 weight % of R32.

7. A propellant filling apparatus (10) of claim 3 wherein the flammable gas comprises at least 98 weight % of R32.

8. A propellant filling apparatus (10) of claim 3 wherein the flammable gas comprises at least 99 weight % of R32.

9. A propellant filling apparatus (10) of claim 3 wherein the flammable gas consists entirely of R152a.

10. A propellant filling apparatus (10) of claim 3 wherein the flammable gas comprises at least 95 weight % of R152a.

11. A propellant filling apparatus (10) of claim 3 wherein the flammable gas consists entirely of a mixture of R152a and R32.

12. A propellant filling apparatus (10) of claim 3 wherein the flammable gas comprises at least 95% by weight of a mixture of R152a and R32.

13. A propellant filling apparatus (10) of claim 3 wherein the flammable gas comprises at least 98% by weight of a mixtures of R152a and R32.

14. A propellant filling apparatus (10) of claim 3 wherein the flammable gas comprises at least 99% by weight of a mixtures of R152a and R32.

15. A propellant filling apparatus (10) of claim 1 wherein the propellant has a global warming potential (GWP) of below 1000.

16. A propellant filling apparatus (10) of claim 1 wherein the propellant has a global warming potential (GWP) of below 700.

17. A propellant filling apparatus (10) of claim 1 wherein the propellant has a global warming potential (GWP) of below 150.

18. A propellant filling apparatus (10) of claim 1 wherein the propellant includes one or more of the following: solvents, surfactants, lubricants, excipients.

19. A propellant filling apparatus (10) of claim 1 supplying in use a said inert gas wherein the inert gas is nitrogen.

20. A propellant filling apparatus (10) of claim 1 wherein the oxygen threshold level of oxygen triggering circulation of inert gas within the filling booth (11) is 9.8%.

21. A propellant filling apparatus (10) of claim 1 wherein the oxygen threshold level of oxygen triggering circulation of inert gas within the filling booth (11) is 7.8%.

22. A propellant filling apparatus (10) of claim 1 wherein the apparatus further comprises a controller for controlling the temperature of the inert gas supply.

23. A propellant filling apparatus (10) claim 1 wherein the apparatus further comprises a controller for controlling the humidity of the inert gas supply.

24. A propellant filling apparatus (10) of claim 1 including a pressure controller (23) that controls the speed of the extraction fan (17), the pressure controller (23) measuring gas pressure in the filling booth (11) and comparing it with atmospheric pressure.

25. A propellant filling apparatus (10) of claim 1 wherein the filling apparatus satisfies "current good manufacturing practices" (cGMP) requirements.

26. A method of operating a propellant filling apparatus (10), the method comprising the steps of filling one or more containers in a filling booth (11) with a propellant;

supplying an inert gas into the filling booth (11);

adjusting the fan speed of an extraction fan (17) to maintain a lower pressure in the filling booth (11) as compared to atmospheric pressure outside the filling booth (11);

detecting levels of oxygen in the filling booth (11); and circulating the inert gas in the filling booth (11) when the detected level of oxygen in the filling booth (11) attains or exceeds a threshold level corresponding to the maximum oxygen concentration of the propellant.

27. The method of operating a propellant filling apparatus (10) of claim 26 wherein the method further comprises the step of detecting the level of inert gas in the filling booth (11).

28. The method of operating a propellant filling apparatus (10) of claim 26 wherein the propellant is Difluoroethane (R152a).

29. The method of operating a propellant filling apparatus (10) of claim 26 wherein the threshold level of oxygen triggering circulation within the filling booth (11) is 9.8%.

30. The method of operating a propellant filling apparatus (10) of claim 26 wherein the threshold level of oxygen triggering circulation within the filling booth (11) is 7.8%.

* * * * *